(12) United States Patent
Shim et al.

(10) Patent No.: US 8,735,077 B2
(45) Date of Patent: May 27, 2014

(54) FET-TYPE BIOSENSOR WITH SURFACE MODIFICATION

(75) Inventors: Jeo-young Shim, Yongin-si (KR); Su-hyeon Kim, Yongin-si (KR); Kyu-tae Yoo, Seoul (KR); Sung-ouk Jung, Suwon-si (KR); Joon-shik Park, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 889 days.

(21) Appl. No.: 11/336,110

(22) Filed: Jan. 20, 2006

(65) Prior Publication Data

US 2006/0205013 A1 Sep. 14, 2006

(30) Foreign Application Priority Data

Jan. 20, 2005 (KR) .................. 10-2005-0005531

(51) Int. Cl.
*G01N 33/53* (2006.01)
(52) U.S. Cl.
USPC .......................................................... 435/7.1
(58) Field of Classification Search
USPC .......................................... 257/244; 435/7.1
See application file for complete search history.

(56) References Cited

U.S. PATENT DOCUMENTS

| | | | |
|---|---|---|---|
| 4,238,757 A | 12/1980 | Schenck | |
| 4,777,019 A | 10/1988 | Dandekar | |
| 5,431,883 A | 7/1995 | Barraud | |
| 5,827,482 A | 10/1998 | Shieh et al. | |
| 6,429,040 B1 | 8/2002 | Bao et al. | ........................ 438/99 |
| 6,602,399 B1 * | 8/2003 | Fromherz et al. | .......... 205/777.5 |
| 2001/0026921 A1 | 10/2001 | Rabbani et al. | |
| 2003/0044997 A1 * | 3/2003 | Kasahara et al. | .............. 436/149 |
| 2003/0138824 A1 | 7/2003 | Makino et al. | ..................... 435/6 |
| 2007/0077596 A1 * | 4/2007 | Krainev et al. | ................. 435/7.1 |

FOREIGN PATENT DOCUMENTS

| | | |
|---|---|---|
| EP | 1 460 130 A1 | 9/2004 |
| EP | 1 542 009 | 6/2005 |
| EP | 1542009 A1 | 6/2005 |

OTHER PUBLICATIONS

NPL documents filed in Apr. 10, 2006 attached here for reference.*
"Potentiometric Detection of DNA Molecules Hybridization Using Gene Field Effect Transistor and Intercalator"; Authors: Toshiya Sakata, et al; Mat. Res. Soc. Symp. Proc. vol. 782; pp. A7.6.1-A7.6.6 (2004).

(Continued)

*Primary Examiner* — Tony Tran
(74) *Attorney, Agent, or Firm* — Cantor Colburn LLP

(57) ABSTRACT

Provided is a field effect transistor (FET) type biosensor including a source electrode, a gate, and a drain electrode. A ligand that can bind to a side of a nucleic acid is added to the surface of the gate. In a conventional FET type biosensor, it is difficult to detect a signal within the debye length because a target nucleic acid is directly fixed to the surface of a gate of the conventional FET. However, in the present invention, this problem can be overcome and the debye length can be increased by treating the surface of a gate of an FET sensor with a ligand that can bind to a side of a nucleic acid. The ligand can be adsorbed onto the surface of the gate. In this case, the nucleic acid is adsorbed parallel to the surface of the gate, not perpendicular to the surface of the gate, thus generating an effective depletion region. In addition, hybridization efficiency can be increased because a hybridized sample can be injected into an FET sensor at high ionic strength.

5 Claims, 13 Drawing Sheets

(56) References Cited

OTHER PUBLICATIONS

European Search Report for Application No. 05027357.2-2204; Date: Mar. 2, 2006.
Korean Intellectual Property Office Action Translation regarding application No. 10-2005-0005531; Date: Jun. 27, 2006.
Taiwan Office Action with English Translation dated Nov. 26, 2008 for Patent Application No. 095102374.
Takenaka, "Synthetic threading intercalators as a new analytical probe for nucleic acid and gene detection," The Japan Society for Analytical Chemistry, (1999), 48(12): 1095-1105.
Murakani, et al., "Immobilization of DNA on Diamond Surface by using Aromatic Compound," The Japan Society of Applied Physics, (The 65th Autumn Meeting, 2004).
Notification of Japanese Office Action 2006-013053.

* cited by examiner

Pyrene

FLUORESCENCE AFTER Cy3 LABELED TARGET BINDING

FLUORESCENCE AFTER Pyrene COATING

FET-TYPE BIOSENSOR WITH SURFACE MODIFICATION

CROSS-REFERENCE TO RELATED PATENT APPLICATIONS

This application claims the benefit of Korean Patent Application No. 10-2005-0005537, filed on 20 Jan. 2005, in the Korean Intellectual Property Office, the disclosure of which is incorporated herein in its entirety by reference.

BACKGROUND OF THE INVENTION

1. Field of the Invention

The present invention relates to a field effect transistor (FET)-type biosensor including a source electrode, a gate electrode, and a drain electrode, and more particularly, to an FET type biosensor in which the surface of a gate is modified to increase sensitivity.

2. Description of the Related Art

As human DNA sequences become known through the completion of the genome project, research into the functions of genes and proteins encoded from genes are being more actively conducted. In response to this active research, the need for development of biosensors that can easily detect biomaterials has increased.

Biosensors that can detect biomaterials using an electric signal are disclosed in U.S. Pat. Nos. 4,238,757; 4,777,019; 5,431,883; 5,827,482; and the like. In particular, U.S. Pat. No. 4,238,757 discloses a field effect transistor (FET) including a source and a drain which is designed to have an antigen reacting to a specific antibody. In this case, the change in the concentration of the antigen in a solution with respect to a drain current was observed over time using the FET.

An FET disclosed in U.S. Pat. No. 4,777,019 includes a gate formed on the doped source and drain regions, and a complementary nucleotide with a nucleotide to be measured is affixed to the gate.

An FET disclosed in U.S. Pat. No. 5,431,883 includes a phthalocayanin thin layer connecting a gate to a drain. Phthalocyanin is an organic insulating material that can be transformed into a conductive material by reacting a chemical sample.

U.S. Pat. No. 5,827,482 discloses a biosensor which includes two FETs which includes molecular receptors bound to gates. The two FETs are arranged in a row to increase sensitivity to different bindings.

FIG. 1 is a schematic diagram of a conventional FET. Referring to FIG. 1, a target oligonucleotide is affixed to the surface of a gate of the FET. FIG. 2 illustrates an increase in the charge accumulation due to binding between an oligonucleotide and a desired complememtary DNA wherein the oligonucleotide is affixed to the surface of the gate of the FET shown in FIG. 1. FIGS. 3A and 3B illustrate the effects of variations in debye length in ImmounoFET. As the size of a molecule affixed to the surface of the gate increases, it is difficult to detect a signal within debye length. Referring to FIG. 3B, when the ionic strength is high, debye length ($d_{Ab}$) is small, and thereby, a signal resulting from a reaction between Ag and Ab is difficult to detect, but when the ionic strength is low, debye Length ($d_{Ab}$) is large, and thus, the signal resulting from the reaction between Ag and Ab can be detected.

Conventional techniques are based on the structure in which an oligonucleotide is affixed to the surface of the FET gate, and such a structure is often used in conventional microarrays. Although the structure does not cause any problems in the microarray, it does in an FET sensor. That is, in the FET sensor, a depletion region is generated from hybridization occurring in the surface of the gate and only charges within the debye length can derive the formation of the depletion region. In order to obtain an effective depletion region, DNA can be arranged parallel to the surface of the gate so that the contact area between DNA and the gate is increased. The parallel structure provides better results when DNA is arranged perpendicular to the surface of the gate. However, surface fixation methods often used in microarrays are used in conventional FET sensors, and thus, an effective depletion region is difficult to obtain. In addition, the fixation of the target oligonucleotide to the surface of the gate results in many disadvantages. For example, when a probe is fixed on the surface of the gate, a long time is required to fix the probe and to perform hybridization in a solution. Typically, DNA hybridization occurs in a solution, but in FET sensors a buffer solution with low ionic strength is used to hybridize DNA to maximize the debye length. The buffer solution with low ionic strength may be preferred for sensors, but results in decreased DNA hybridization efficiency. That is, the hybridization occurring on the surface of the gate is decreased and low signals are generated.

When attempting to overcome these problems in conventional techniques, the inventors of the present invention have confirmed that when the surface of a gate of an FET sensor is modified, a DNA backbone is adsorbed at the surface of the gate, and signals can be effectively detected within the debye length.

SUMMARY OF THE INVENTION

The present invention provides an FET type biosensor that induces charges of the nucleic acid more closer to a surface of a gate of an FET by modifying the surface of the gate, and thus increasing sensitivity.

According to an aspect of the present invention, there is provided the FET type biosensor including a source electrode, a gate electrode, and a drain electrode, in which a ligand that can bind to a side of a nucleic acid is added to the surface of the gate electrode.

Any FET used in conventional biosensors, CMOS devices, or the like can be used in the present invention. For example, n-MOS or p-MOS can be used as the FET. The source electrode may provide a carrier, such as a free electron or a hole, the drain electrode receives the carrier provided by the source electrode, and the gate electrode controls the flow of the carrier between the source electrode and the drain electrode. FIG. 1 illustrates a simple structure of the FET. The FET type biosensor is preferably used to measure the fixation or hybrization of the nucleic acid, such as DNA, in an electrolyte, and can detect hybridization without labeling.

In the present invention, the nucleic acid may be in parallel to the surface of the gate of the FET due to adding of the ligand that can bind to the side of the nucleic acid into the surface of the gate so that a DNA backbone is adsorbed most adjacent to the surface of the gate. As a result, a signal of a nucleic acid hybridization can be easily detected within the debye length. That is, a depletion region below a gate insulator can be effectively formed, thus forming n-type or p-type channel between the source electrode and the drain electrode.

The ligand does not bind to an end of a single-stranded or a double-stranded nucleic acid, but binds to the side of the nucleic acid through non-covalent bonding. Probably, the ligand may be an intercalator that is bound by hydrophobic interaction or the like between stacked base pairs of the nucleic acid, or a groove binder that is bound by hydrogen bonding to major or minor groove of the helical structure of the nucleic acid. Although the ligand can bind to a double strand and a single strand, binding to the double strand results in higher thermodynamical stability. That is, there are the hybridized double strand and the non-hybridized single strand, the ligand is binding only to the hybridized double strand, such that the present FET can act as a sensor.

In the biosensor according to the present invention, the intercalator may include any ligand that can be bound through a hydrophobic interaction or the like between stacked base-pairs of the nucleic acid. Probably, the ligand can be a non-ionic aromatic compound. In this case, when the ligand has a positive charge, any nucleic acid with a negative charge, regardless of whether it is a single nucleic acid or a double-stranded nucleic acid, can bind to the positive ligand and when the ligand has a negative electrode, the binding of the nucleic acid is prevented by the repulsive force between identical electric charges. That is, the ligand may be non-ionic. In addition, the ligand can also be an aromatic compound suitable for intercalating between the stacked hydrophobic bases. The intercalator may be naphthalene, anthracene, pyrene, phenanthren, acridine derivatives, daunomycin, or the like.

In the biosensor according to the present invention, the groove binder may include any ligand that can bind to the major or minor groove of the helical structure of the nucleic acid through hydrogen bonding or the like. Preferably, the ligand comprises at least two hydrogen bonding sites for enough bonding. The major groove binder may be methyl green, or the like, and the minor groove binder may be netropsin, berenil, distamycin A, DAPI, or the like.

In the biosensor according to the present invention, the surface of the gate can be composed of any material to which the ligand that can bind to the side of the nucleic acid can bind, for example, gold, $SiO_2$, $TiO_2$, and $Al_2O_3$. A modified thiol group of the intercalator or the groove binder can bind to gold; and a modified silane or carboxylic acid group of the intercalator or the groove binder can bind to $SiO_2$, $TiO_2$, or $Al_2O_3$.

In the biosensor according to the present invention, the nucleic acid may be hybridized in a solution and then bind to the ligand that can bind to the side of a double-stranded nucleic acid and may be located on the surface of the gate. In a conventional biosensor, first, a single strand probe nucleic acid of a double-strand nucleic acid to be hybridized is affixed to the surface of the gate through the covalent bonding and then hybridization occurs on the surface of the gate. However, in the biosensor according to the present invention, the probe nucleic acid is not directly fixed to the surface of the gate through covalent bonding. Instead, the probe nucleic acid is hybridized with a target nucleic acid in a solution in a same or different reservoir, and then added to the surface of the gate.

In the conventional biosensor, a long time is required to fix the probe and to hybridize the probe with the single strand nucleic acid in a solution. In consideration of the debye length, typically, a signal of an FET is measured at low ionic strength, which is not desirable for hybridization. The hybridization according to the present invention is performed in aspects to hybridization efficiency and the debye length.

In the biosensor according to the present invention, the nucleic acid may be various nucleic acids, similar nucleic acids, or a combination of these, and may be selected from DNA, RNA, peptide nucleic acid (PNA), locked nucleic acid (LNA), and a combination of these.

BRIEF DESCRIPTION OF THE DRAWINGS

The above and other features and advantages of the present invention will become more apparent by describing in detail exemplary embodiments thereof with reference to the attached drawings in which:

FIG. 11 is a graph of a drain current with respect to time of a conventional FET which does not include an intercalator or the like.

DETAILED DESCRIPTION OF THE INVENTION

Figure 1:
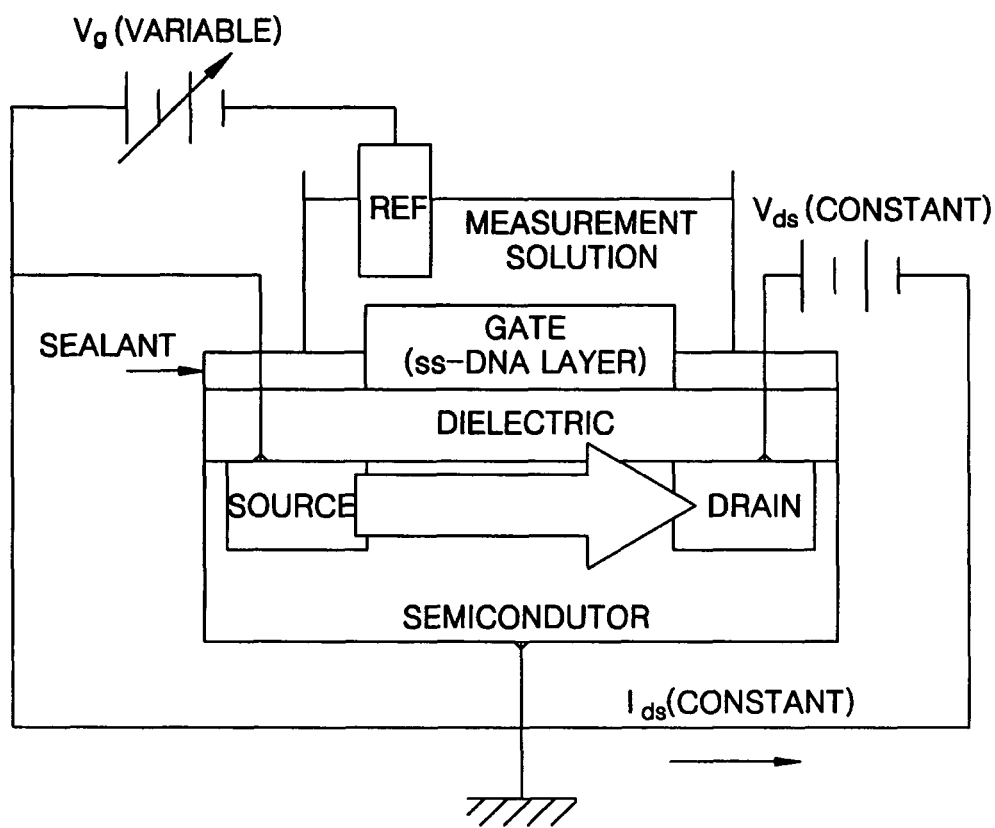
FIG. 1 is a schematic diagram of a conventional field effect transistor (FET)
Figure 2:
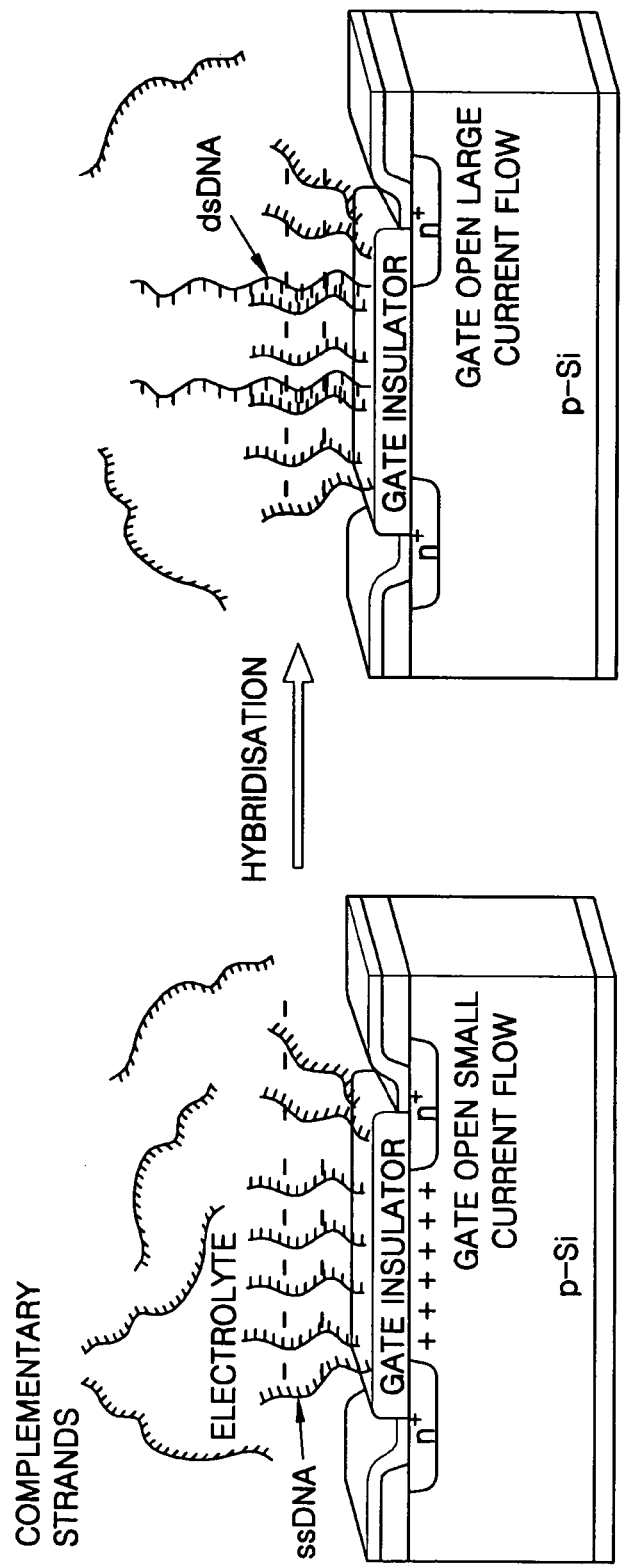
FIG. 2 illustrates binding between an oligonuleotide affixed to the surface of the gate of the FET and a desired complementary DNA.
Figure 3A:
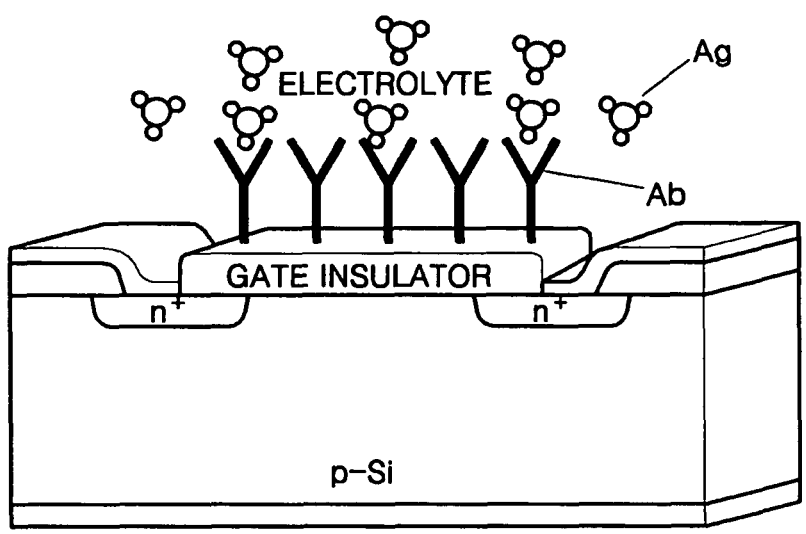
FIGS. 3A and 3B illustrate the relationship between debye length and ionic strength.
Figure 3B:
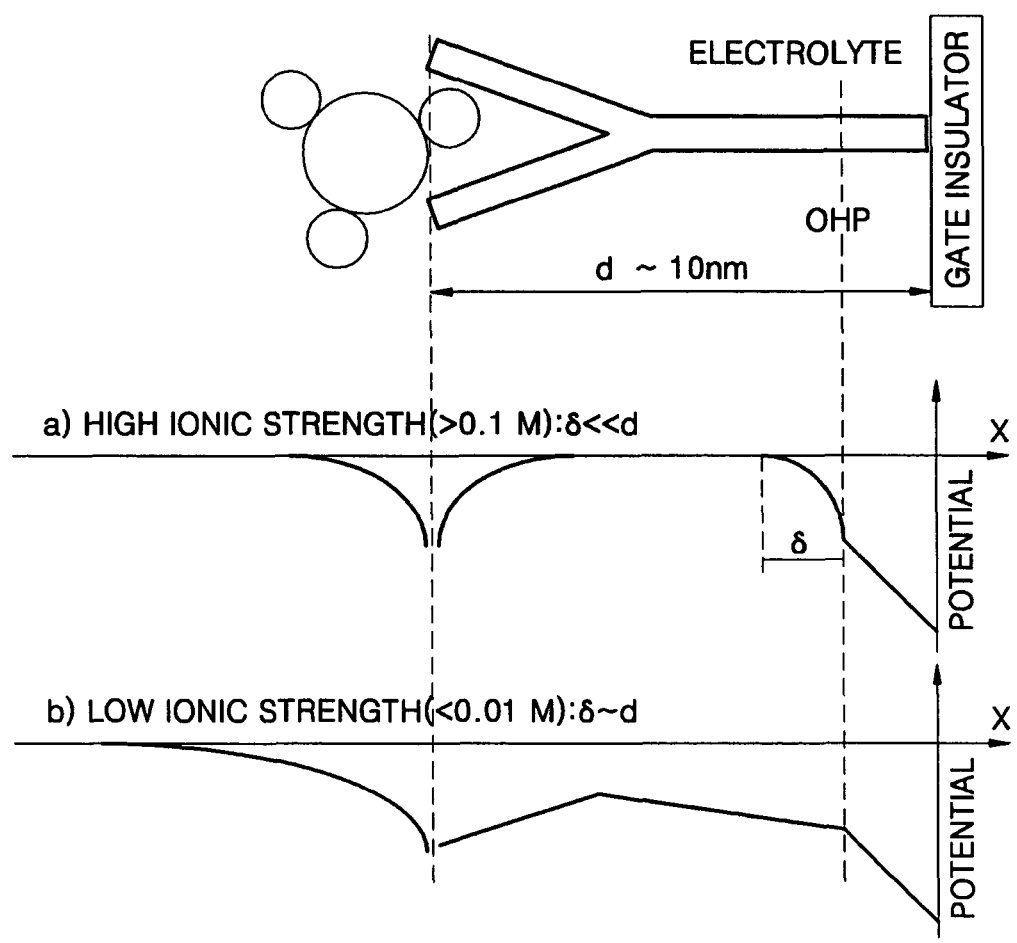
Figure 4A:
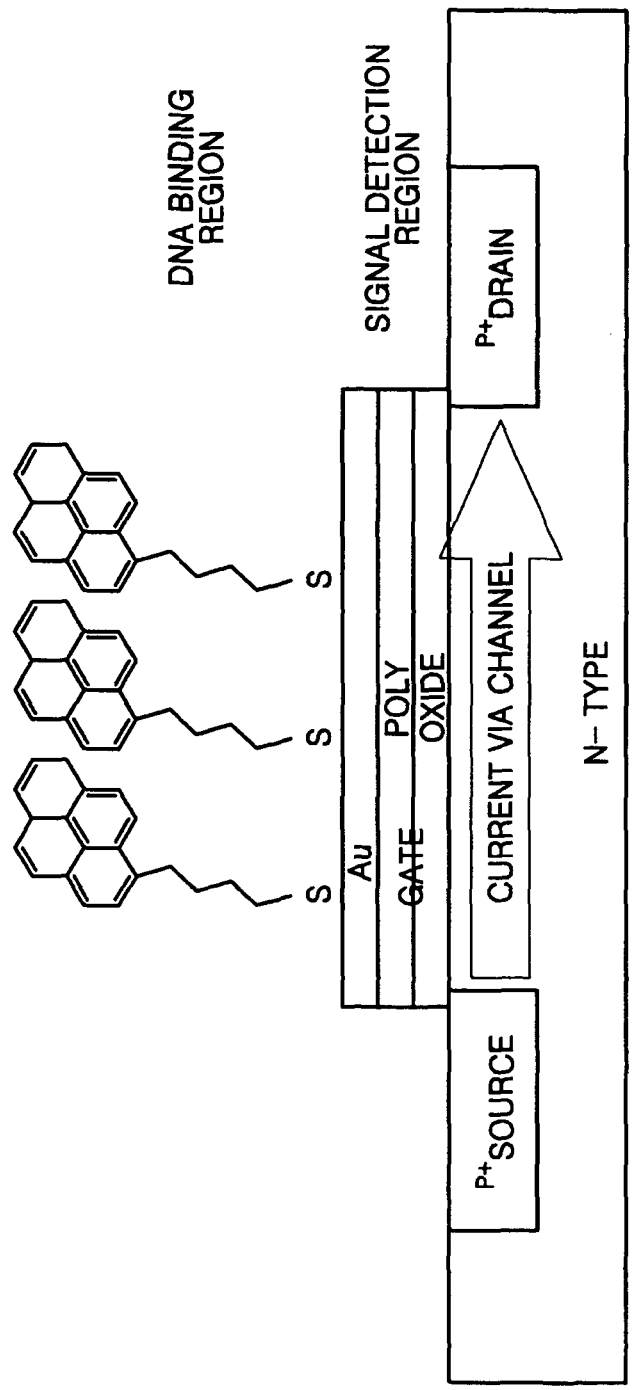
FIG. 4A is a schematic view of an FET type biosensor according to an embodiment of the present invention.
Figure 4B:
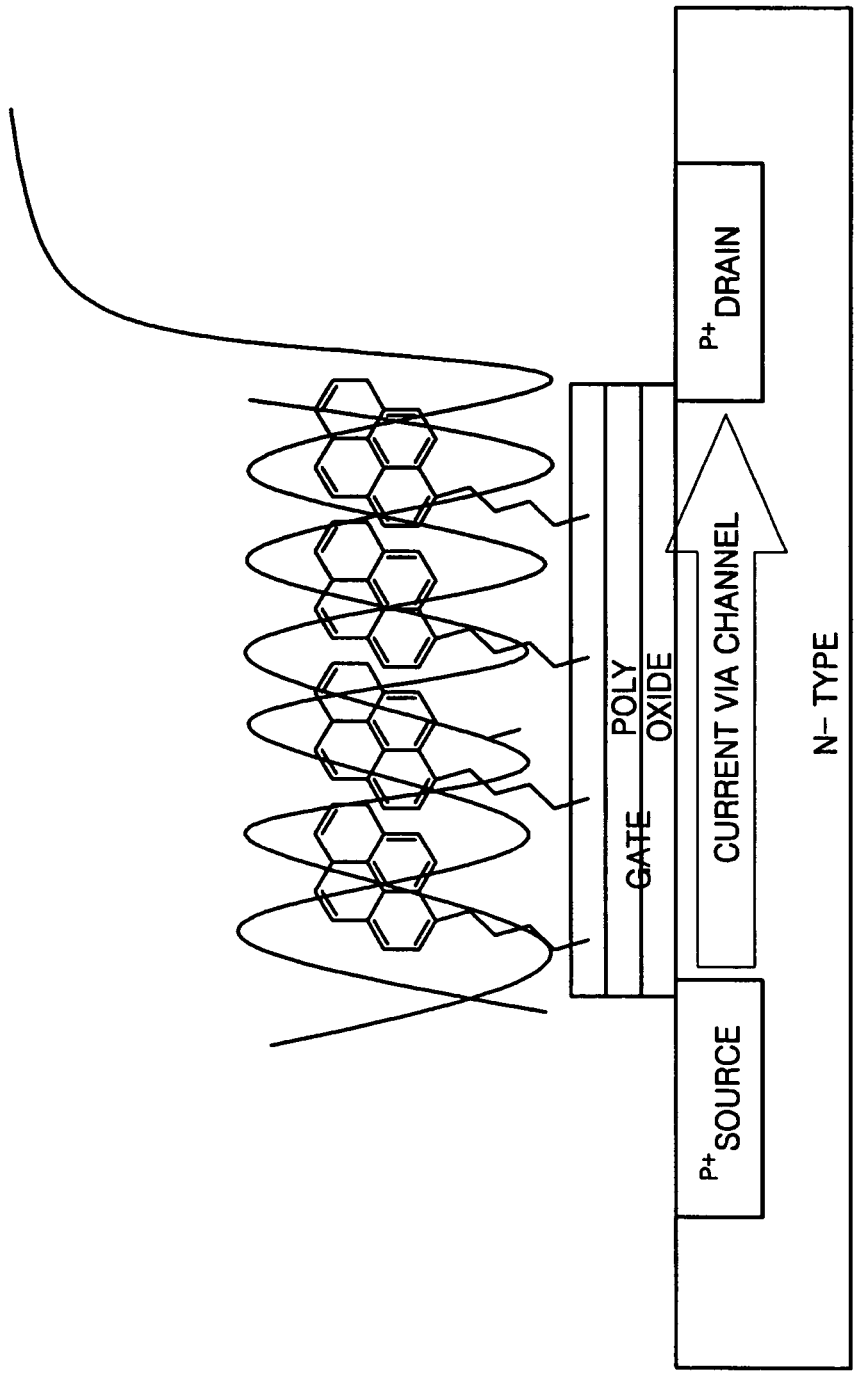
FIG. 4B is a view of the FET type biosensor shown in FIG. 4A when a double-stranded nucleic acid is bound to the biosensor.

FIG. 4A is a schematic view of an FET type biosensor according to an embodiment of the present invention, and FIG. 4B is a view of the FET type biosensor shown in FIG. 4A when a double-stranded nucleic acid is bound to the biosensor. The FET type biosensor includes a DNA binding region to which DNA is bound, and a signal detection region where a signal generated due to the charge of DNA is measured. In the DNA binding region, an intercalator, a groove binder, or the like is bound to the surface of a gate composed of gold, $SiO_2$, $TiO_2$, or the like. The signal detection region has an FET structure including a source, a drain, and a gate electrode. According to an embodiment of the present invention, the double-stranded DNA is adsorbed parallel to the surface of the gate through the intercalator or the groove binder so that effective depletion region can be formed.

Figure 5:
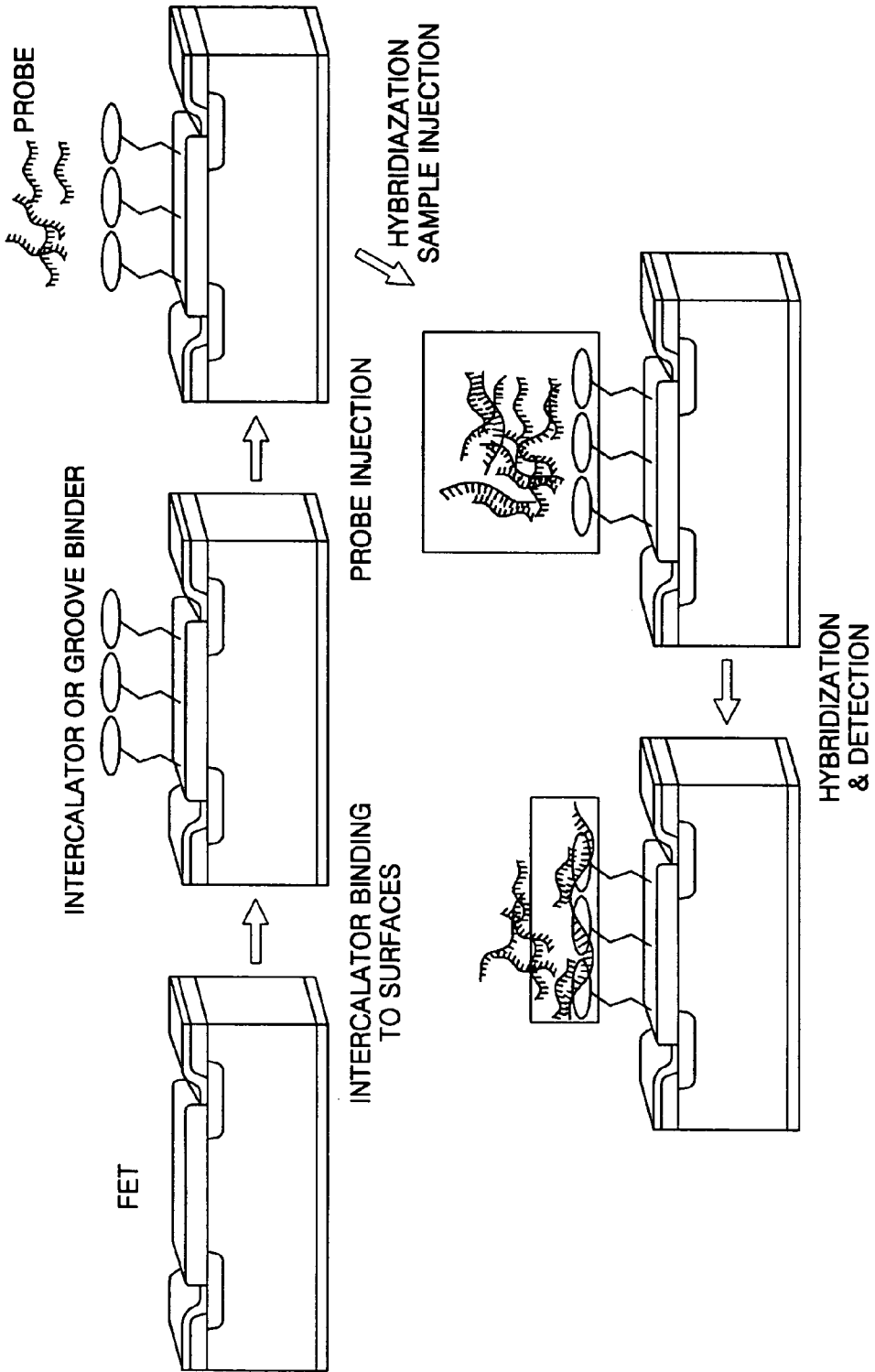
FIG. 5 illustrates a process of detecting hybridization of a nucleic acid using the FET type biosensor shown in FIG. 4A.

FIG. 5 illustrates a process of detecting the hybridization of a nucleic acid using the FET type biosensor shown in FIG. 4A. Referring to FIG. 5, the intercalator or groove binder is attached to the surface of the gate of the FET, a probe is injected, a hybridization sample is injected to hybridize the probe with the hybridization sample, and the resulting product is bound to the intercalator or the groove binder. As a result, the charge can be focused within the debye length, thus effectively increase the signal to noise ratio (SNR) of hybridization.

The biosensor according to the present embodiment is formed by etching the surface of a silicon substrate through photolithography or by attaching a separately assembled biosensor to the surface of the substrate. The substrate may be composed of silicon, glass, fused silica, plastic, PDMS, or the like.

A method of manufacturing a biosensor according to an embodiment of the present invention will be described in detail. First, an oxide layer is formed on the semiconductor substrate, a micro chamber or micro channel where reaction is to take place is formed by etching the surface of the substrate, impurity regions are formed by doping the side walls or a bottom of the micro chamber or the micro channel with impurities, and the resulting substrate is etched with an etching liquid to remove portions of the impurity regions formed on the side walls or the bottom, thus defining a channel region. Subsequently, an oxide layer is formed on the channel region, and a gate electrode composed of gold is formed in the channel region, thus completing the biosensor. The gate electrode of the FET may be a gold thin film, and a ligand that can be attached to a side of a nucleic acid by a thiol group is attached to the surface of the gate using a self assembled monolayer method.

The present invention will now be described in detail with reference to exemplarily embodiments. The invention, however, should not be construed as being limited to the embodiments set forth herein.

EMBODIMENT 1

In the present embodiment, a coupling agent such as GAPS was bound to a silicon substrate including a 1000 Å $SiO_2$ layer, and an intercalator was added thereto. The addition of the intercalator was confirmed using a fluorescent scanner, and an oligonucleotide with a complementary sequence was hybridized and fixed to the substrate through the intercalator. Intercalation of the hybridized oligonucleotide was confirmed using a fluorescence scanner.

1) Bonding Between Silicon Substrate and Coupling Agent (GAPS)

First, a substrate was cleaned before a surface treatment was performed. In the cleaning process, a pure acetone and water and then a piranha solution, which is formed by mixing a hydrogene peroxide and a sulfonic acid in a weight ratio of 1:3 were used to remove organic impurities. Then, the resulting substrate was cleaned using a large amount of water and acetone and then dried. In detail, the substrate cleaning process was performed using a wet station used in a semiconductor manufacturing process, the piranha solution treating process was performed using a sulfuric acid bath, and the cleaning process using water was performed through QDR. At this time, the substrate was fixed in a silicon wafer carrier composed of Teflon. After the cleaning, the substrate was spin-dried.

After the cleaning, the substrate was spin coated with a solution of 20% by volume of ɤ-aminopropyltriethoxy silane (GAPS) dissolved in ethanol or with a solution of 20% by volume of ɤ-aminopropyldiethoxy silane (GAPDES) using a spin coater (CEE 70 obtained from CEE Inc.). The spin coating was initially performed at 500 rpm/10 sec, and then mostly at 2000 rpm/10 sec. After the spin coating was completed, the substrate was fixed to a Teflon wafer carrier, and then hardened at 120° C. for 40 minutes. The hardened substrate was immersed in water for 10 minutes, washed with ultrasonic waves for 15 minutes, immersed in water for 10 minutes, and then spin dried. The dried substrate was cut into a square or rectangle. All of these processes were performed in a cleanroom-class 1000 in which dust particles are sufficiently eliminated.

2) Addition of Intercalator

The silicated substrate was coated with an intercalator. Pyrene was used as the intercalator, and the coating was achieved by immersion. First, an immersion solution (0.5 g Pyrene/200 ml+0.1 ml Triethylamine) was manufactured by dissolving 1-pyrenebutyric acid N-hydroxysuccinimide ester (Pyrene) in a solution of methylene chloride (MC). The immersion solution and the substrate were reacted with each other at room temperature for 5 hours in a reaction container. After the reaction was completed, the resulting substrate was taken from the immersion solution, washed using MC three times for 10 minutes each time and then using ethanol three times for 10 minutes each time, and then dried. The amount of pyrene that was reacted with the substrate was quantified using a fluorescent scanner (GenePix 4000B obtained from Axon Inc.) At this time, 532 nm light was radiated and the intensity of fluorescence was obtained at 570 nm.

3) Intercalation of Oligonucleotide and Substrate with Intercalator

Figure 6:
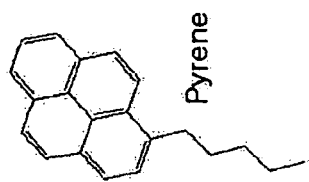
FIG. 6 is a fluorescent image obtained after binding with pyrene and a fluorescent image obtained after binding with cy3-labeled oligonucleotide.
Figure 6:
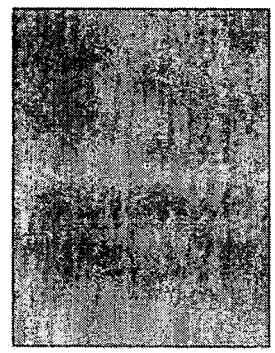
Figure 6:
Figure 6:
Figure 7A:
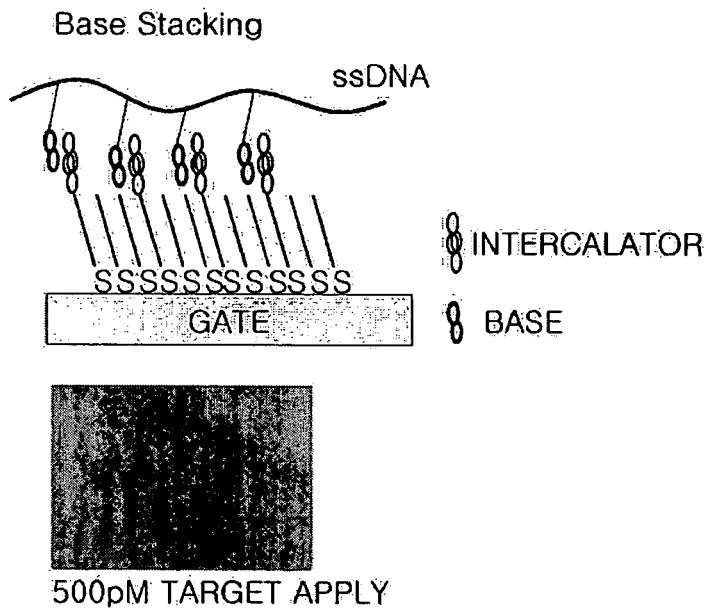
FIG. 7A illustrates ssDNA base-stacked to an intercalator of the biosensor shown in FIG. 4A.
Figure 7B:
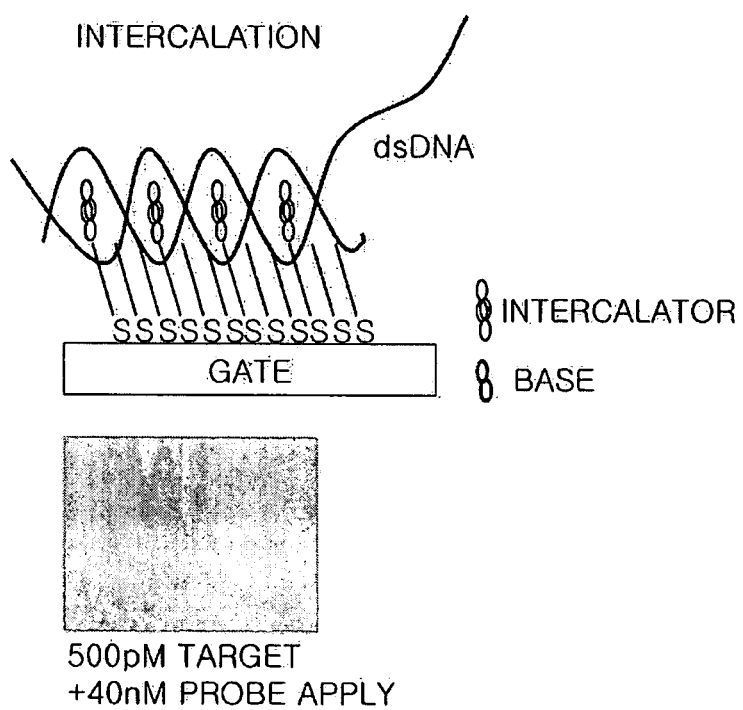
FIG. 7B illustrates dsDNA intercalated to the biosensor shown in FIG. 4B.

A hybridized oligonucleotide was intercalated with pyrene coated on the substrate. In detail, a cy3-labeled oligonucleotide was hybridized with a complementary oligonucleotide, and then the hybridized oligonucleotide was intercalated with pyrene coated on the substrate. The cy3-labeled oligonucleotide had a base sequence of CAA GAC AAG AGA ACA, and the complementary oligonucleotide had a base sequence of TGT TCT CTT GTC GTT. After the cy3-labeled oligonucleotide was hybridized with the complementary oligonucleotide for 1 hour, the hybridized oligonucleotide was experienced intercalation on the pyrene-coated substrate for 3 hours. After the intercalation reaction was completed, the substrate was cleaned and the amount of the hybridized oligonucleotide that was intercalated was measured. FIG. 6 is a fluorescent image obtained after binding with pyrene and a fluorescent image obtained after binding with cy3-labeled oligonucleotide. Referring to FIG. 6, effective intercalation was confirmed for both case. FIG. 7A illustrates ssDNA base-stacked to an intercalator of the biosensor shown in FIG. 4A, and FIG. 7B illustrates dsDNA intercalated to the biosensor shown in FIG. 4B. As illustrated in FIG. 7A, the addition of only ssDNA as a target resulted in the formation of background phosphorescence, thus confirming that ssDNA was base-stacked, but, as illustrated in FIG. 7b, more intense fluorescence was observed when dsDNA was intercalated, thus confirming that the intercalator according to the present embodiment was well combined with double-stranded nucleic acid.

EMBODIMENT 2

The change of an electric signal was observed by adding an intercalator to the surface of a gate of an FET device. In the present embodiment, N-Pyrene-2-aminoethanthiol (pyrenethiol) was synthesized and used to modified the surface of the gate. Pyrenethiol contains a thiol functional group and pyrene. Pyrenethiol can be fixed to the surface of the gate due to the functional group, and can also be intercalated with an oligonucleotide or DNA due to the pyrene. Any FET that is commercially used can be used in the present invention. However, in the present embodiment, the FET had a gate on which gold was deposited, which was manufactured by Samsung Semiconductor Inc.

1) Washing of FET Device

The FET device according to the present embodiment is different form a conventional FET device in that gold was deposited on the gate so that pyrenethiol could be added to the surface of the gate using Au—S bonding. First, organic impurities in the FET device were removed using a piranha solution formed by mixing hydrogen peroxide and sulfonic acid in a weight ratio of 1:3. Then, the resulting FET device was washed with a large amount of water and dried.

2) Identification of Pyrenethiol Bonding Using Electric Signal

Figure 8:
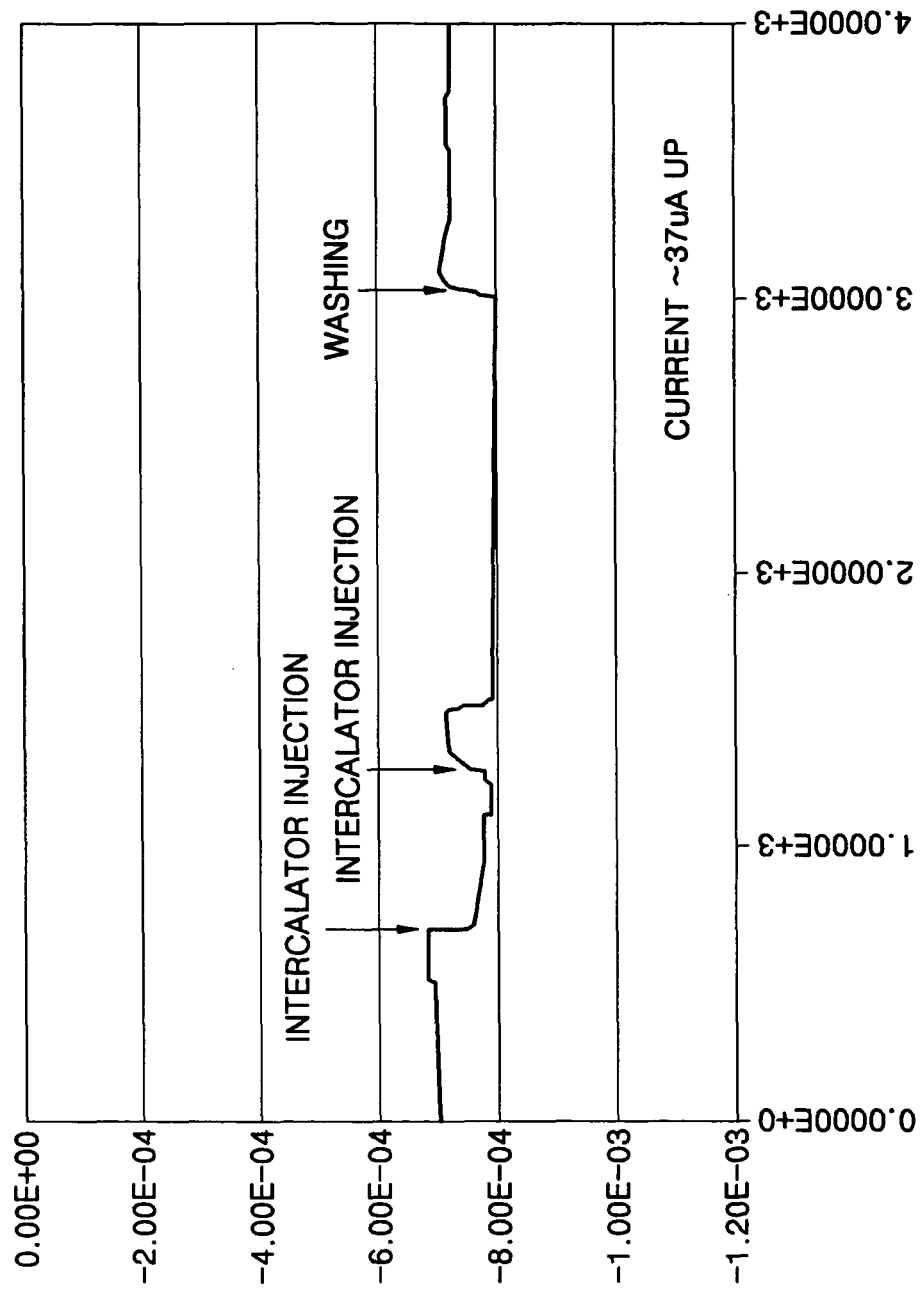
FIG. 8 is a graph of current with respect to time when an intercalator (pyrenethiol) was added to the surface of an FET.

The dried FET device was connected to a parameter analyzer, and stabilized in a 0.1×PBS. When the FET device was stabilized, pyrenethiol was added to the 0.1×PBS solution. An increase in a current due to the thiol functional group at the end of the pyrenethiol was measured. When the change of the current due to the terminated thiol functional group stabilized, the FET device was cleaned using 0.1×PBS. The current measured after the cleansing was larger the current measured before binding with pyrenethiol, which indicates that pyrenethiol was successfully bound to the surface of the gate. FIG. 8 is a graph of current with respect to time when the intercalator (pyrenethiol) was added to the surface of the FET.

EMBODIMENT 3

In the present embodiment, the surface of a gate of an FET device was modified with an intercalator to locate DNA very closed to the surface of the gate thus inducing a substantial change of a signal. Pyrenethiol was used to modify the surface of the gate. In order to observe the change of the electrical signal due to the binding of an oligonucleotide, a complementary pair of oligonucleotides and a non-complementary pair of oligonucleotides were used.

1) Addition of Intercalator to FET Device

The intecalator was added to the gate of the FET device. Since the FET device included a gate treated with gold, which is difference from a conventional FET, the intercalator could be added to the surface of the gate through Au—S bonding. First, First, organic impurities in the FET device were removed using a piranha solution formed by mixing hydrogen peroxide and sulfonic acid in a weight ratio of 1:3. Then, the resulting FET device was washed with a large amount of water and dried. The washed FET device was immersed in a solution formed by mixing pyrenethiol and mecaptopropanol in a weight ratio of 1:2, washed with ultrasonic waves in a methylene chloride solution for 2 minutes, and then dried.

2) Electric Detection Using FET Device when PM

Figure 9:
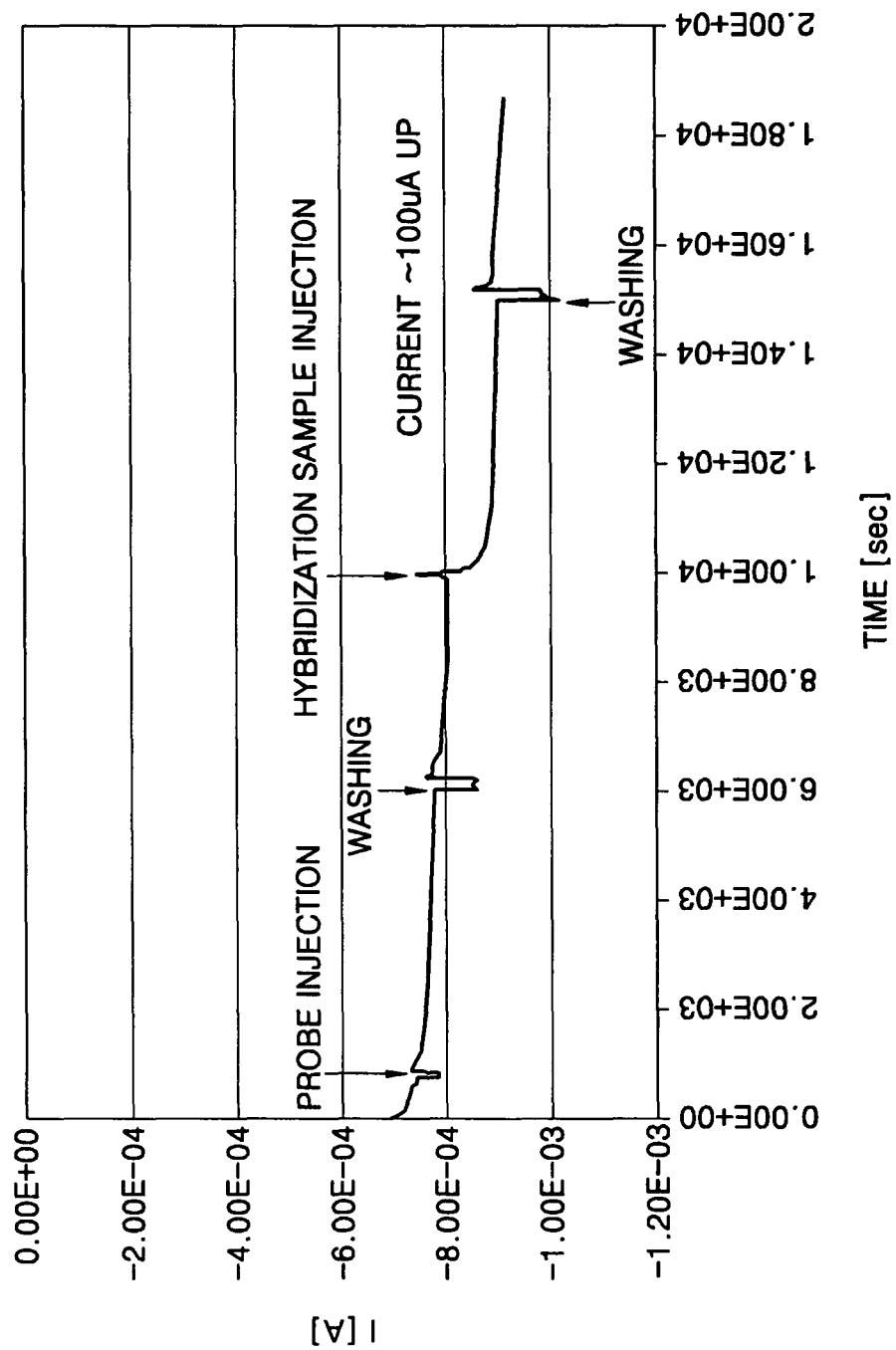
FIG. 9 is a graph of current with respect to time when hybridized DNA with a complementary base sequence was injected into the surface of the FET with the intercalator.

The FET device was connected to a parameter analyzer, and then immersed in a solution of 0.1×PBS for stabilization when applying various voltages. In the present embodiment, 2V was applied to the gate. When the FET device was stabilized, 400 pM of a probe oligonucleotide was injected into the FET device. The probe oligonucleotide had a base sequence of 3'-TGT TCT CTT GTC TTG-5'. In this case, a small change in an electric signal was observed. When the signal is stabilized, the FET device was washed with the solution of 0.1×PBS. When the current was stabilized again after the washing, a solution with a hybridized complementary oligonucleotide was injected. The injected oligonucleotides had base sequences of 3'-TGT TCT CTT GTC TTG-5' and 3'-CAA GAC AAG AGA ACA-5' and concentrations of 400 pM and 40 nM, respectively. In this case, the hybridized oligonucleotide had a double-stranded structure so that intercalation could be achieved. The current increased substantially, and was washed using the solution of 0.1×PBS after stabilization was obtained. FIG. 9 is a graph of current with respect to time when DNA with a complementary base sequence was injected into the surface of the FET with the intercalator.

3) Electric Detection Using FET Device when MM

Figure 10:
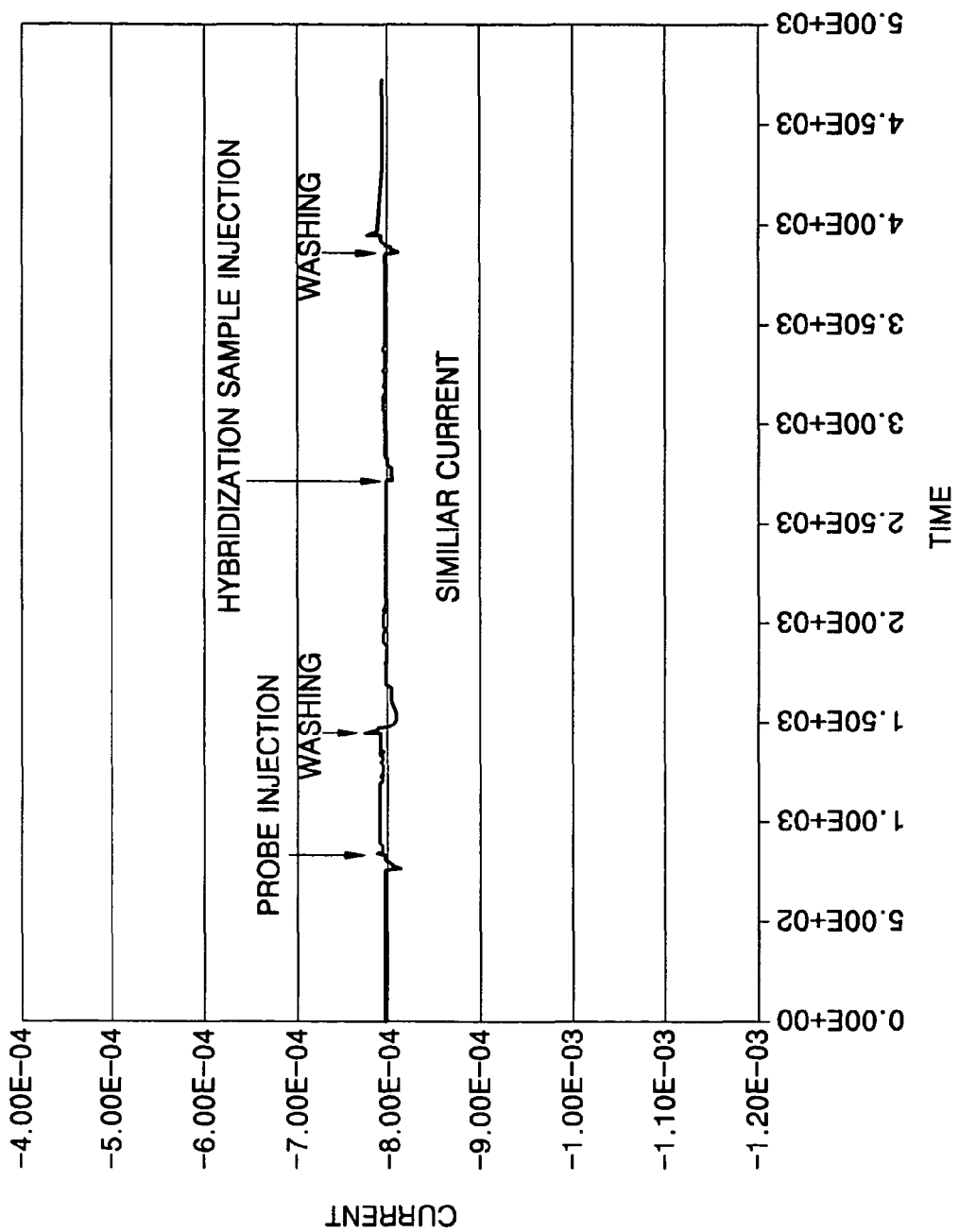
FIG. 10 is a graph of current with respect to time when DNA with a non-complementary base sequence was injected into the surface of the FET with the intercalator.

The FET device was connected to a parameter analyzer, and then immersed in a solution of 0.1×PBS for stabilization when applying various voltages. In the present embodiment, 2V was applied to the gate. When the FET device was stabilized, 400 pM of a probe oligonucleotide was injected into the FET device. The probe oligonucleotide had a base sequence of 3'-TGT TCT CTT GTC TTG-5'. In this case, a small change in an electric signal was observed. When the signal is stabilized, the FET device was washed with the solution of 0.1×PBS. When the current was stabilized again after the washing, a solution with a hybridized non-complementary oligonucleotide was injected. The injected oligonucleotides had base sequences of 3'-TGT TCT CTT GTC TTG-5' and 3'-GCG CTG AGC TGG TGG GC-5' and concentrations of 400 pM and 40 nM, respectively. In this case, however, a double-stranded structure was not formed because the oligonucleotides were non complementary to each other although the oligonucleotides were hybridized, thus failing to generate intercalation. The current was almost unchanged, and the FET device was washed with the solution of 0.1×PBS after stabilization was competed. FIG. 10 is a graph of current with respect to time when DNA with a non-complementary base sequence was injected into the surface of the FET with the intercalator.

Figure 11:
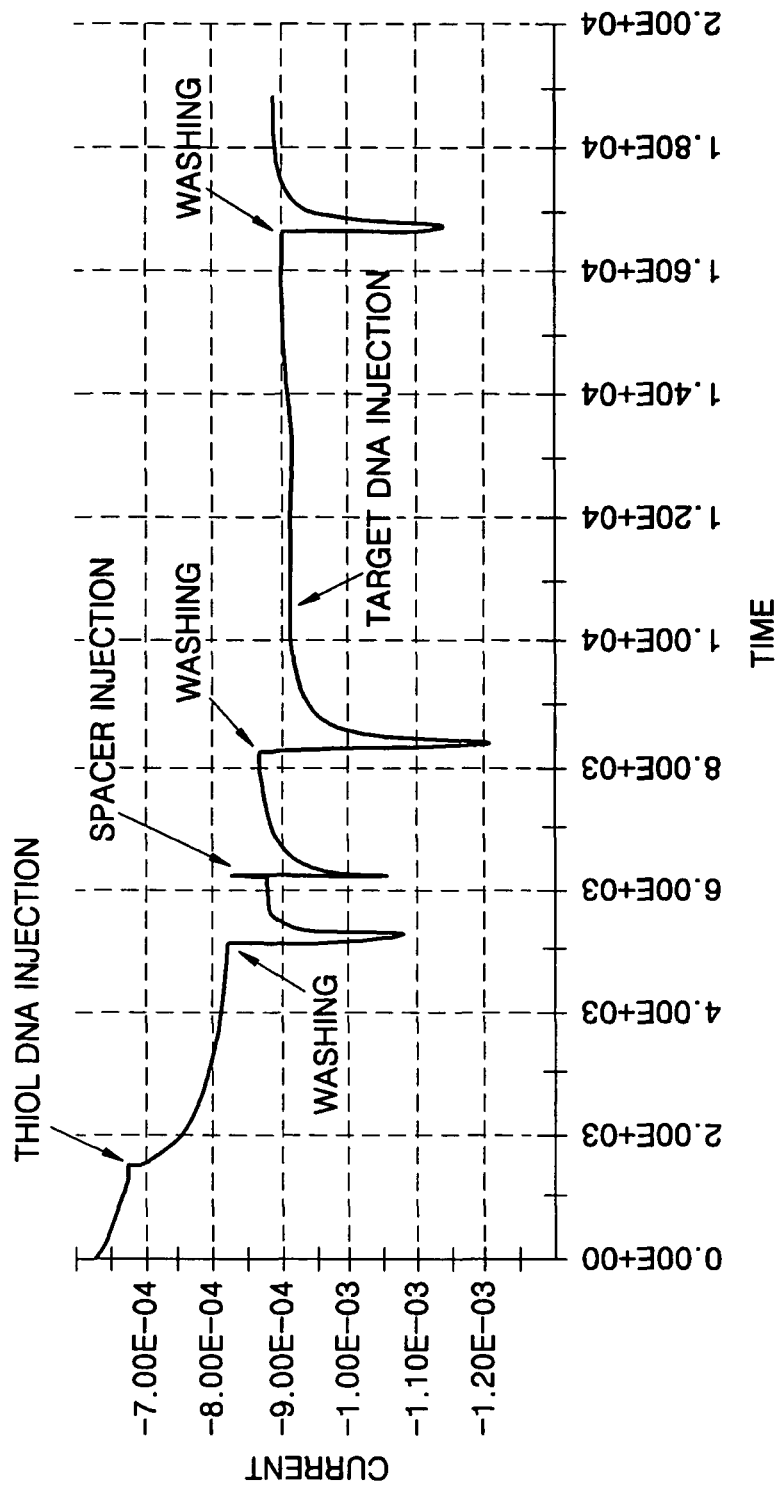

Meanwhile, a conventional FET to which an intercalator or the like was not added was used in the same manner as the present embodiment to detect electric signals. FIG. 11 is a graph of current with respect to time of the conventional FET. When thiol was reacted with DNA, the current was increased by 202 uA, after the spacer (thiol) reaction, the current was increased by 40 uA, and after hybridization, the current was decreased by 28 uA. Typically, the current increases when a reaction occurs within the debye length. However, the current of the conventional FET was decreased on the contrary to the FET in embodiments of the present invention. That is, the reaction between thiol and DNA was induced within the debye length and the current was decreased, but after hybridization, the change of in the signal was abnormal.

As described above, in a conventional FET type biosensor, it is difficult to detect a signal within the debye length because a target nucleic acid is directly affixed to the surface of a gate of an FET. However, in the present invention, this problem can be resolved and the debye length can be increased by treating the surface of a gate of an FET sensor with a ligand that can bind to a side of a nucleic acid. The ligand can selectively combine with the side of the nucleic acid so that the nucleic acid existing in a solution can be adsorbed onto the surface of the gate. In this case, the nucleic acid is adsorbed parallel to the surface of the gate, not perpendicular to the surface of the gate, thus generating effective depletion region. In addition, hybridization efficiency can be increased because a hybridized sample can be injected into an FET sensor at high ionic strength.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A field effect transistor (FET) type biosensor comprising
a source electrode,
a gate electrode,
a drain electrode, and
an intercalator covalently attached to the surface of the gate electrode.

2. The FET type biosensor of claim 1, wherein the surface of the gate electrode is composed of a material selected from the group consisting of gold, $SiO_2$, $TiO_2$ and $Al_2O_3$.

3. The FET type biosensor of claim 1, wherein a nucleic acid is hybridized in a solution and then added to the intercalator covalently attached to the surface of the gate electrode.

4. The FET type biosensor of claim 3, wherein the nucleic acid is selected from the group consisting of DNA, RNA, PNA, LNA, and a combination of these.

5. The FET type biosensor of claim 1, wherein the intercalator is selected from the group consisting of naphthalene, anthracene, pyrene, and phenanthren.

* * * * *